United States Patent [19]

Tietze et al.

[11] Patent Number: 5,132,416
[45] Date of Patent: Jul. 21, 1992

[54] KETOPHOSPHAMIDE GLYCOSIDES

[75] Inventors: Lutz F. Tietze, Goettingen; Roland Fischer, Bovenden; Matthias Beller, Goettingen, all of Fed. Rep. of Germany

[73] Assignee: Bayer Aktiengesellschaft, Leverkusen, Fed. Rep. of Germany

[21] Appl. No.: 570,191

[22] Filed: Aug. 20, 1990

[30] Foreign Application Priority Data

Aug. 30, 1989 [DE] Fed. Rep. of Germany ....... 3928659

[51] Int. Cl.$^5$ ................. C07H 11/04; C07H 13/00; C07H 15/00
[52] U.S. Cl. .................. 536/117; 536/17.9; 536/17.2; 536/18.4; 536/4.1
[58] Field of Search ............. 536/117, 17.9, 18.4, 536/17.2; 514/23, 25

[56] References Cited

U.S. PATENT DOCUMENTS

| | | | |
|---|---|---|---|
| 4,062,909 | 12/1977 | Morgan et al. | 536/117 |
| 4,086,302 | 4/1978 | Morgan et al. | 536/117 |
| 4,841,085 | 6/1989 | Farquhar et al. | 558/180 |
| 4,908,356 | 3/1990 | Borch et al. | 544/72 |

FOREIGN PATENT DOCUMENTS

0345583 12/1989 European Pat. Off. .

OTHER PUBLICATIONS

Liebigs Annalen Der Chemie, vol. 1990, No. 2, Feb. 1990, pp. 151–157, Weinheim, DE.; L. F. Tietze et al.: "Novel stable bioactivated cyclophosphamide derivatives for selective cancer chemotherapy synthesis of aldophosphamide acetal-glycosides and their glycoconjugates".

Angewandte Chemie International Edition in English, vol. 29, No. 7, Jul. 1990, pp. 782–783, Weinheim, DE.; L. F. Tietze et al.: "Development of tailor-made cytostatics activable by acid-actalyzed hydrolysis for selective tumor therapy".

Carbohydrate Research, vol. 194, Dec. 1989, pp. 155–162, Amsterdam, NL; L. F. Tietze et al.: "Stereoselective synthesis of 1,1-dialkyl-1-methoxy-methyl glucosides (acetal-glucosides)", p. 156.

Carbohydrate Research, vol. 180, 1988, pp. 253–262, Amsterdam, NL; L. F. Tietze et al.: "Stereoselective synthesis of (1-alkoxyalkyl) alpha- and beta-D-glucopyranosiduronates (acetal-glucopyranosiduronates): A new approach to specific cytostatics for the treatment of cancer", p. 253 "Abstract"; p. 255.

*Primary Examiner*—Johnnie R. Brown
*Assistant Examiner*—Everett White
*Attorney, Agent, or Firm*—Sprung Horn Kramer & Woods

[57] ABSTRACT

Compounds of the formula (I)

$$R^1-O-\underset{\underset{OR^2}{|}}{\overset{\overset{R^3}{|}}{C}}-CH_2-CH_2-O-\underset{\underset{NH_2}{|}}{\overset{\overset{O}{\|}}{P}}-N(CH_2CH_2Cl)_2 \quad (I)$$

wherein $R^1$ represents a pyranosyl radical and $R^4$, $R^2$, and $R^3$ are as specified herein, compositions containing the compounds, methods of using the compounds to selectively kill tumor cells, and a process for the preparation of the compounds.

5 Claims, No Drawings

KETOPHOSPHAMIDE GLYCOSIDES

The invention relates to new acid-labile ketal glycosides of aldophosphamide, to a process for their preparation and to their use as highly selective cytostatics in cancer therapy.

It is known that malignant cells show increased glycolysis and thus lactate production compared to the normal tissue and that the pH in tumor tissue can be decreased by intravenously administered glucose (compare S. Tanneberger, Experimentelle und klinische Tumorchemotherapie; Allgemeine Tumorchemotherapie [Experimental and Clinical Tumour Chemotherapy; General Tumour Chemotherapy]; G. Fischer Verlag, Stuttgart/New York 1980; Naturwiss 46, 2(1959); Cancer Res. 42, 1498 (1982); 42, 1505 (1982)).

In the past, it has been attempted to utilize these differences in the pH between normal and tumor tissue for selective tumor therapy (Compare Liebigs Ann. Chem. 1987, 847–856; Tetrahedron Lett. 22 (1981) 239–242). An attempt had been made to convert alkylating compounds, which owing to a too small differentiation between healthy and malignant tissue have a very small therapeutic breadth, into non-toxic, acid-labile prodrug forms which are only selectively cleaved to the active alkylating cytostatic in the tumor tissue owing to the reduced pH prevailing there Selective tumor therapy is supposed to have been attempted in this manner.

However, it has been shown that the compounds prepared in the abovementioned literature source do not prove to be so acid-labile that they are selectively cleaved back again to the active cytocidal agents in the tumor tissue.

It has now surprisingly been ascertained that the compounds mentioned in the following are non-toxic, whereas they can be converted by hydrolysis into cytocidal compounds at the pH achievable in tumor tissue as a result of hyperglycaemia.

The new compounds correspond to the general formula (I)

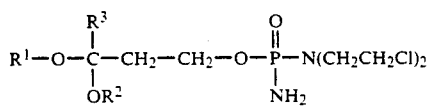

in which
$R^1$—represents a pyranosyl radical of the formula

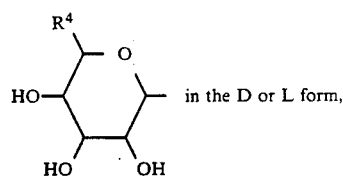

in which
$R^4$—denotes the group of the formula —$CH_2OH$ or straight-chain or branched alkyl having up to 4 carbon atoms,
where the OH functions of the sugar are optionally protected,
$R^2$—represents straight-chain or branched alkyl having up to 8 carbon atoms and
$R^3$—represents straight-chain or branched alkyl having up to 10 carbon atoms.

Preferred compounds of the general formula (I) are those in which
$R^1$—represents a hexopyranosyl radical of the formula

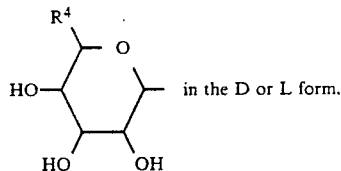

in which
$R^4$—denotes the group of the formula —$CH_2OH$ or methyl,
where the OH functions of the sugar are optionally protected,
$R^2$—represents straight-chain or branched alkyl having up to 6 carbon atoms and
$R^3$—represents straight-chain or branched alkyl having up to 8 carbon atoms.

Particularly preferred compounds of the general formula (I) are those in which
$R^1$ represents the D-glucopyranosyl radical, where the OH functions of the sugar are optionally protected,
$R^2$—represents straight-chain or branched alkyl having up to 4 carbon atoms and
$R^3$—represents straight-chain or branched alkyl having up to 6 carbon atoms.

Suitable OH protecting groups are the customary protecting groups such as methylbenzoyl, benzoyl, acetyl or benzyl. Benzyl, acetyl or methylbenzoyl are preferred. Acetyl (Ac) is particularly preferred.

In addition, a process for the preparation of the compounds of the general formula (I) according to the invention has been found, which is characterized in that compounds of the general formula (II)

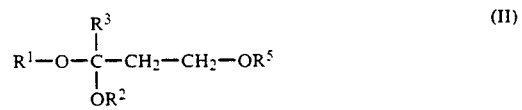

in which
$R^1$, $R^2$ and $R^3$ have the abovementioned meaning and
$R^5$—represents a typical hydroxyl protecting group, are first converted, with removal of the protecting group by known methods, into the compounds of the general formula (III)

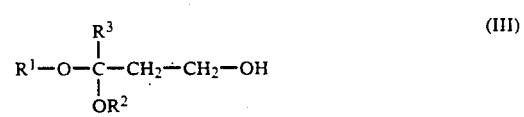

in which
$R^1$, $R^2$ and $R^3$ have the abovementioned meaning, then reacted with N,N-bis(2-chloroethyl)-dichlorophosphoramide of the formula (IV)

in inert solvents, in the presence of a base, subsequently carrying out an ammonolysis and, if appropriate, removing the protecting groups on the sugar radical.

The process according to the invention can be illustrated by the following equation:

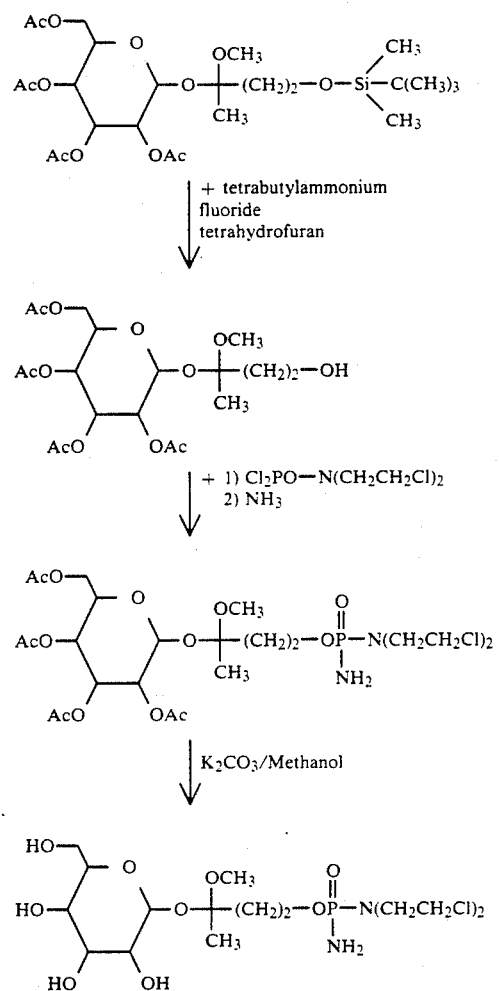

A hydroxyl protecting group in the context of the abovementioned definition of $R^5$ in general represents trimethylsilyl, triethylsilyl, triisopropylsilyl, tert.butyldimethylsilyl, tert.butyl-diphenylsilyl, benzyl, 2-nitrobenzyl, acetyl (Ac) or trifluoromethoxy. Tert.-butyldimethylsilyl, tert.butyl-diphenylsilyl and acetyl are preferred.

The removal of the protecting group is carried out in a manner known per se, for example in the case of the silyl groups by means of tetrabutylammonium fluoride or by hydrogenolytic cleavage, if $R^5$ represents the benzyl group, with hydrogen in the presence of a catalyst, in an inert solvent [compare in addition Th. Greene: "Protective Groups in Organic Synthesis", J. Wiley & Sons, 1981, New York].

Suitable solvents are customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or mineral oil fractions, or halogenated hydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoramide, acetonitrile, acetone or nitromethane. It is also possible to use mixtures of the solvents mentioned. Tetrahydrofuran and dichloromethane are preferred.

The customary inert organic solvents which do not change under the reaction conditions are suitable for reaction with the compound of the formula (IV). These preferably include benzene, toluene, xylene, dichloromethane or dimethylformamide. It is also possible to use mixtures of the solvents mentioned. Dichloromethane is particularly preferred.

Suitable bases are sodium hydride, potassium hydride, imidazole, tetrazole and the customary organic amines. These preferably include alkylamines such as triethylamine, diisopropylamine, dicyclohexylamine and ethyl diisopropylamine. Triethylamine is particularly preferred.

The bases are in general employed in an amount of 1 to 5 moles, preferably 1 to 3 moles, relative to the compounds of the formula (IV).

The reaction is in general carried out at normal pressure. However, it is also possible to carry out the process at elevated pressure or at reduced pressure (for example in a range from 0.5 to 5 bar).

The process according to the invention is in general carried out in a temperature range from 0° C. to +60° C., preferably at room temperature.

The abovementioned reaction conditions are also unchanged during the ammonolysis. The solvent evaporated by the passage of the stream of ammonia is replaced during the reaction.

The removal of the protective groups on the sugar radical is carried out by customary methods in inert solvents in the presence of a base or by hydrogenolysis.

Suitable bases for the removal are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonates, or alkali metal alkoxides such as sodium ethoxide, sodium methoxide, potassium ethoxide, potassium methoxide or potassium tert.butoxide. Sodium carbonate or potassium carbonate are particularly preferably employed.

Suitable solvents for the removal are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferred. It is also possible employ mixtures of the solvents mentioned.

The removal is in general carried out in a temperature range from 0° C. to +100° C., preferably from +20° C. to +80° C.

In general, the removal is carried out at normal pressure. However, it is also possible to work at elevated pressure or at reduced pressure (for example from 0.5 to 5 bar).

N,N-Bis(2-chloroethyl)-dichlorophosphoramide of the formula (IV) is known [compare J. Am. Chem. Soc. 76, 655 (1954)].

The compounds of the general formula (II) are new and can be prepared by reacting compounds of the general formula (V)

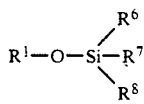

(V)

in which
R[1] has the abovementioned meaning and
R[6], R[7] and R[8] are identical or different and represent $C_1$-$C_8$-alkyl or phenyl,
first with compounds of the general formula (VI)

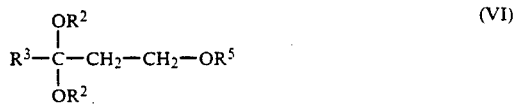

(VI)

in which
R[2], R[3] and R[5] have the abovementioned meaning and
R[2], has the abovementioned meaning of R[2] and is identical to or different from this
and then reacting with the ketone of the general formula (VII)

(VII)

in which
R[3] and R[5] have the abovementioned meaning, on which the compound (VI) is based, in inert solvents, if appropriate in the presence of a catalyst.

Suitable solvents are the abovementioned inert solvents. Dichloromethane is preferred.

Suitable catalysts are Lewis and Brönsted acids such as trifluoroacetic acid, p-toluenesulphonic acid, camphorsulphonic acid, trimethylsilyl trifluoromethane-sulphonate and iodotrimethylsilane. In general, 0.01 to 1, preferably 0.05 to 0.5 moles of catalyst, are employed relative to 1 mole of reaction component.

The compounds of the general formula (VII) are in general employed in an amount from 1 to 10 moles, preferably of 3 moles, relative to 1 mole of the compounds of the general formulae (V) and (VI).

The process is in general carried out in a temperature range from $-78°$ C. to $+20°$ C., preferably at $-78°$ C.

The compounds of the general formula (V) are known [compare W. A. Bonner, J. Org. Chem. 26, 908 (1961); L. Vargha and J. Kurzmann, Chem. Ber. 96, 2016 (1963)].

The compounds of the general formulae (VI) and (VII) are also known or can be prepared by customary methods [compare J. Org. Chem. 26, 908, 1961 and Can. J. Chem. 56, 2889, 1978, Heterocycles 15, 999 (1981); Chem. Pharm. Bull. 15, 1893 (1967)].

The compounds according to the invention show an unforeseeable, useful spectrum of pharmacological activity.

The acid-labile glycosides of the inactivated cyclophosphamide of the general formula (I) represent, for the first time, a cytostatic which is non-toxic in its transport form. At the pH achievable in the tumor tissue by means of hyperglycaemia, they liberate a cytocidal compound, the Friedman acid, by hydrolysis.

The compound to be cleaved (Example 5) was dissolved in 1 ml of water (double-distilled). Each 200 μl was added to 1 ml of a buffer system which was thermostated at 37° C. Experiments were carried out at the following pH values: 5.0, 5.5, 6.0, 6.5 and 7.0. The cleavages were investigated after 1 h, 2 h, 4 h, 8 h, 24 h and then at intervals of 24 h using NMR spectroscopy. The concentrations of the phosphate buffer systems used were 0.05 mol/l.

Cleavage experiments which were carried out according to the abovementioned working procedure show that the compound from Example 5 is preferably cleaved at pH=6 with a half-life of 4 h.

The new active compounds can be converted in a known way into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration from about 0.5 to 90% by weight of the total mixture, i.e. in amounts which are sufficient in order to achieve the dosage range indicated.

The formulations are produced, for example, by extending the active compounds with solvents and/or excipients, if appropriate using emulsifiers and/or dispersants, it being possible, for example, in the case of the use of water as diluents to use, if appropriate, organic solvents as auxiliary solvents.

Examples of auxiliaries which may be mentioned are: water, non-toxic organic solvents, such as paraffins (for example mineral oil fractions), vegetable oils (for example groundnut/sesame oil), alcohols, for example ethyl alcohol, glycerol), excipients, such as, for example, ground natural minerals (for example kaolins, aluminas, talc, chalk), ground synthetic minerals (for example highly disperse silica, silicates), sugars, for example sucrose, lactose and dextrose), emulsifiers, for example polyoxyethylene fatty acid esters, polyoxyethylene fatty alcohol ethers), dispersing agents (for example lignin-sulphite waste liquors, methylcellulose, starch and polyvinylpyrrolidone) and lubricants (for example magnesium stearate, talc, stearic acid and sodium sulphate).

Administration is carried out in a customary manner, preferably orally or parenterally, in particular perlingually or intravenously. In the case of oral administration, tablets can of course also contain additions, such as sodium citrate, calcium carbonate and dicalcium phosphate together with various additives, such as starch, preferably potato starch, gelatin and the like in addition to the excipients mentioned. Furthermore lubricants, such as magnesium stearate, sodium lauryl-sulphate and talc may additionally be used for tabletting. In the case of aqueous suspensions, various flavor enhancers or colourants can be added to the active compounds in addition to the abovementioned auxiliaries.

On oral administration, those pharmaceutical preparations are to be used in which the liberation of the active compounds takes place first in the intestine. Liberation in the stomach can lead to undesired premature acidolysis of the substances according to the invention.

In the case of parenteral administration, solutions of the active compounds can be employed using suitable liquid excipient materials.

In general, it has proved advantageous on intravenous administration to administer amounts of about 0.001 to 1 mg/kg, preferably about 0.01 to 0.5 mg/kg of body weight to attain effective results, and on oral administration the dosage is about 0.01 to 20 mg/kg, preferably 0.1 to 10 mg/kg of body weight.

In spite of this it may be necessary to deviate from the amounts mentioned, in particular depending on the body weight or the manner of administration, but also in the light of the disorder and its individual behavior towards the medicaments or the manner of its formulation and the point in time or interval at which administration takes place. Thus, in some cases it may be sufficient to manage with less than the previously mentioned minimum amounts, while in other cases the upper limit mentioned must be exceeded. In the case of the administration of relatively large amounts, it may be advisable to divide these into a number of individual doses over the course of the day.

The application of compounds of the general formula I, in which R' represents a D-glucopyranosyl radical, to cultures of mammary carcinoma cells resulted in very slight toxicity at a pH of 7.4, whereas the survival rate of the cancer cells at a pH of 6.2 was decreased by a factor of $5 \times 10^{-5}$.

On administering one single dose of 500 mg/kg of the abovementioned compound to Sprague Dowly rats carrying a transplanted AH-13r tumour, complete remission of the tumour occurred.

STARTING COMPOUNDS

Example I 4-tert.Butyldiphenylsiloxybutan-2-one

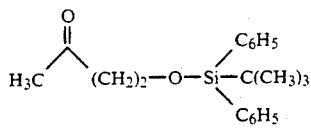

7.43 (109 mmol) of imidazole and 20 g (72.8 mmol) of tert.butyldiphenylsilyl chloride were dissolved in 200 ml of dichloromethane and cooled to 0° C. 7.69 g (87.4 mmol) of 4-hydroxybutan-2-one were added dropwise to this solution. After warming to room temperature, the mixture was stirred for 12 hours (TLC checking). The reaction mixture was extracted twice by shaking with 80 ml of ice water, the organic phase was dried using sodium sulphate and, after evaporating the solvent, the residue was distilled in an oil pump vacuum. 22.3 g (68.4 mmol) of product were obtained.

Yield: 94% of theory R=0.29 (tert.butyl methyl ether/petroleum ether 1:8) B.p.=127–130/0.06 Torr M.p.=38°–40° C. $C_{20}H_{26}O_2S$; (326.51)

Calc.: C 73.57 H 8.03. Found: C 73.59 H 8.16.

Example II 4-tert.Butyldimethylsiloxybutan-2-one

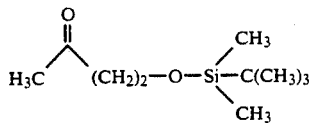

The compound was prepared in analogy to the procedure of Example I.

Yield: 92% of theory $R_f$=0.34 (tert.butyl methyl ether/petroleum ether 1:8) B.p.=63° C./15 Torr $C_{10}H_{22}O_2Si$ (202.37)

Calc.: C 59.35 H 10.96. Found: C 59.32 H 10.80.

Example III 4-(tert.Butyldiphenylsiloxy)-2,2-dimethoxybutane

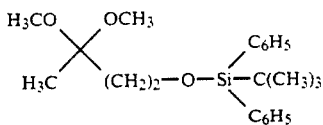

The ketalization was carried out according to E. C. Taylor and L. S. Chiang, Synthesis, 1977, 457.

Yield: 78% of theory M.p.: 28°–30° C. $R_f$=0.44 (tert.butyl methyl ether/petroleum ether 1:8) B.p.: 145°–150° C./0.05 Torr $C_{22}H_{32}O_3Si$ (372.58)

Calc.: C 70.92 H 8.66. Found: C 70.96 H 8.65.

Example IV 4-(tert.Butyldimethylsiloxy-2,2-dimethoxybutane)

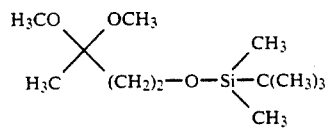

The title compound was prepared in analogy to the procedure of Example III.

Yield: 86% of theory $R_f$=0.48 (tert.butyl methyl ether/petroleum ether 1:8) B.p.=75° C./15 Torr $C_{22}H_{28}O_3Si$ (248.43)

Calc.: C 58.02 H 11.36. Found: C 58.18 H 11.30.

PREPARATION EXAMPLES

Example 1

(1'RS)-3'-Diphenyl-tert.butylsiloxy-1'-methoxy-1'-methylpropyl-2,3,4,6-tetra-O-acetyl-β-D-glucopyranoside

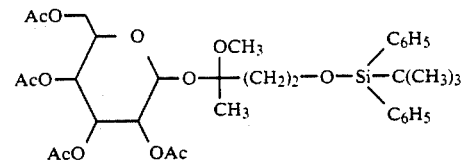

420 mg (1.00 mmol) of 1-O-trimethylsilyl-2,3,4,6-tetra-O-acetyl-β-D-glucopyranoside was dissolved in 15–20 ml of dichloromethane and 980 mg (3.00 mmol) of the compound from Example I and 373 mg (1.00 mmol) of the compound from Example III were added under protective gas (argon) and with the exclusion of moisture. After cooling to −78° C., 20 mol % of trimethylsilyl trifluoromethanesulphonate (TMS triflate) were added and the mixture was stirred at this temperature until the reaction was complete (TLC checking). The reaction was terminated by adding 1 ml of a mixture of triethylamine and ethanol (1:1). Subsequent rapid column filtration of the cold solution over about 5 g of silica gel (eluent tert.butyl methyl ether) and evaporation of the solvent in vacuo yielded the crude product. Further purification was carried out by flash chromatography on 50 g of silica gel (eluent: tert.butyl methyl ether/petroleum ether/triethylamine 100:100:0.7). After concentrating the collected fractions, the substance was dried at room temperature in a high vacuum and stored under protective gas at $-20°$ C. until further use. 269 mg (0.39 mmol) of the title compound were obtained as a colorless oil.

Yield: 39% of theory $R_f=0.41$ (tert.butyl ether/petroleum ether 2:1) $C_{35}H_{48}O_{12}Si$ (688.8)

Calc.: C 61.03 H 7.02. Found: C 61.06 H 7.11.

Example 2

(1'R,S)-3'-Dimethyl-tert.butylsiloxy-1'-methoxy-1'-methylpropyl-2,3,4,6-tetra-O-acetyl-$\beta$-D-glucopyranoside

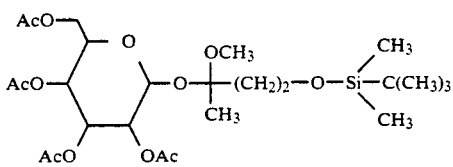

The title compound was prepared in analogy to the procedure of Example 1.

Yield: 28% of theory $R_f=0.48$ (ethyl acetate/petroleum ether 1:1) $C_{25}H_{14}O_{12}Si$ (564.70)

Calc.: C 53.17 H 7.85. Found: C 53.51 H 8.01.

Example 3

(1'R,S)-3'-Hydroxy-1'-methoxy-1'-methylpropyl-2,3,4,6-tetra-O-acetyl-$\beta$-D-glucopyranoside

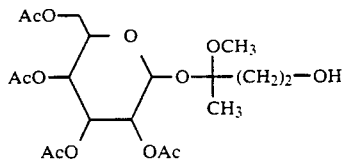

269 mg (0.39 mmol) of the compound from Example 1 were dissolved in 5 ml of tetrahydrofuran and a suspension of 96 mg of tetrabutylammonium fluoride$\times$3 H$_2$O (dried for 2 hours in a high vacuum at room temperature before the reaction) in 5 ml of tetrahydrofuran were added at room temperature. The reaction mixture was stirred at 4° C. until conversion was complete (TLC checking, reaction time about 4-6 hours). The solvent was then removed in vacuo and the crude product was flash chromatographed on 25 of silica gel (32-63 $\mu$m, eluent: dichloromethane/petroleum ether-/ethanol 15:5:1 containing 0.7% triethylamine). 165 mg (0.37 mmol) of a colorless oil are obtained.

Yield: 94% of theory $R_f=0.27$ (dichloromethane/petroleum ether/ethanol 20:5:1) $C_{19}H_{30}O_{12}$ (450.4)

Calc.: C 50.66 H 6.71. Found: C 50.59 H 6.76.

Example 4

(3 RS, RS-P)-[3-Methoxy-3-(2,3,4,6-tetra-O-acetyl-$\beta$-D-glucopyranosyloxy)butyl]-N,N-bis-(2-chloroethyl)-phosphoric acid diamidate

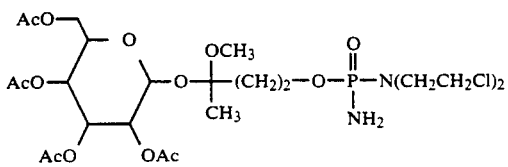

490 mg (1.09 mmol) of the compound from Example 3 were dissolved in 15 ml of dichloromethane with the exclusion of moisture and under protective gas and 3 ml of triethylamine and 1.13 g (4.35 mmol) of bis-(2-chloroethyl)-dichlorophosphoramide were added. The mixture was stirred at room temperature (TLC checking) for 36 hours. A vigorous stream of dry ammonia was then passed through the solution for 1.5 hours (evaporated solvent is replaced). The resulting precipitate is separated by flash column filtration over about 10 g of silica gel (dichloromethane/petroleum ether/ethanol 20:5:1 containing 0.7% of triethylamine). After evaporating the solvent in vacuo, the crude product is purified by flash chromatography on 50 g of silica gel (32-63 $\mu$m, dichloromethane/petroleum ether/ethanol 20:5:1 containing 0.7% of triethylamine). 501 mg (0.81 $\mu$mol) of a slightly yellow crystalline foam remain.

Yield: 74% of theory $R_f=0.24$ (dichloromethane/petroleum ether/ethanol 3:1:1) $C_{23}H_{39}Cl_2N_2O_{13}P$ (653.44)

Calc.: C 42.28 H 6.04 N 4.29. Found: C 42.69 H 6.22 N 4.76.

Example 5

(3 RS-P) 3-Methoxy-3-($\beta$-D-glucopyranosyloxy)butyl]-N,N-bis-(2-chloroethyl)-phosphoric acid diamidate

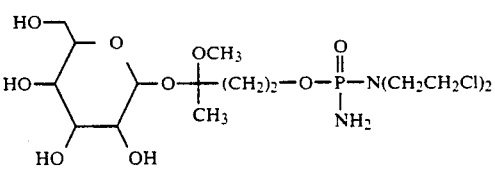

25 mg of activated potassium carbonate are added to a solution of 501 mg (0.81 mmol) of peracetylated ketophosphamide acetal glucoside (4) in 5 ml of methanol. The mixture is stirred for about 10 minutes (TLC checking; it is then diluted with 10 ml of tert.butyl methyl ether and the solution is rapidly filtered through 10-15 g of celite. After removing the solvent in vacuo, 349 mg (0.72 mmol) of a yellow crystalline foam remain.

Yield: 89% of theory $R_f=0.30$ (methylene chloride/-petroleum ether/ethanol 3:1:1)

$C_{15}H_{31}Cl_2N_2O_9P$ (485.30)

Calc.: C 37.12 H 6.44 N 5.77. Found: C 37.35 H 6.42 N 5.94.

It is understood that the specification and examples are merely illustrative but not limitative of the present invention and that other embodiments within the spirit and scope of the invention will suggest themselves to those skilled in the art.

We claim:

1. A compound of the formula (I)

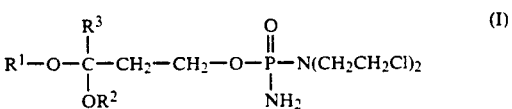

in which

R$^1$ represents a pyranosyl radical of the formula

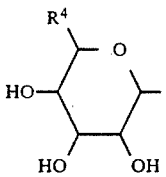

in which

R[4] represents —CH$_2$OH or straight-chain or branched alkyl having up to 4 carbon atoms;

R[2] represents straight-chain or branched alkyl having up to 8 carbon atoms; and R[3] represents straight-chain or branched alkyl having up to 10 carbon atoms;

the OH functional groups of the pyranosyl radical being unprotected or protected with a hydroxy protecting group selected from the group consisting of methylbenzoyl, benzoyl, acetyl or benzyl.

2. The compound according to claim 1, wherein

R[4] represents —CH$_2$OH or methyl;

R[2] represents straight-chain or branched alkyl having up to 6 carbon atoms; and R[3] represents straight-chain or branched alkyl having up to 8 carbon atoms.

3. The compound according to claim 1, wherein R[1] represents the D-glucopyranosyl radical;

R[2] represents straight-chain or branched alkyl having up to 4 carbon atoms; and R[3] represents straight-chain or branched alkyl having up to 6 carbon atoms.

4. The compound according to claim 1, which is (3 RS, RSP)-[3-methoxy-3-(2,3,4,6-tetra-O-acetyl-β-D-glucopyranosyloxy)butyl]-N,N-bis-(2-chloroethyl)-phosphoric acid diamidate of the formula

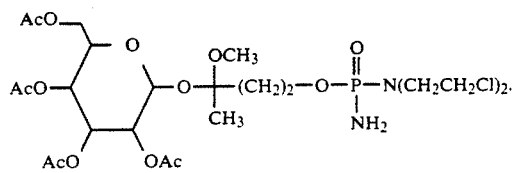

5. The compound according to claim 1, which is (3 RS, RSP)-[3-methoxy-3-(β-D-glucopyranosyloxy)-butyl]-N,N-bis-(2-chloroethyl)-phosphoric acid diamidate of the formula

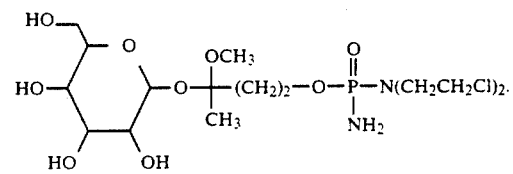

* * * * *